US009833781B2

(12) United States Patent
Huang et al.

(10) Patent No.: US 9,833,781 B2
(45) Date of Patent: Dec. 5, 2017

(54) ELECTRIC CONTROLLED MICRO-FLUIDIC DEVICE

(71) Applicant: IMEC, Leuven (BE)

(72) Inventors: Chengjun Huang, Leuven (BE); Chengxun Liu, Leuven (BE); Liesbet Lagae, Leuven (BE); Paolo Fiorini, Brussels (BE); Benjamin Jones, Kessel-Lo (BE)

(73) Assignee: IMEC, Leuven (BE)

( * ) Notice: Subject to any disclaimer, the term of this patent is extended or adjusted under 35 U.S.C. 154(b) by 482 days.

(21) Appl. No.: 14/280,595

(22) Filed: May 17, 2014

(65) Prior Publication Data

US 2014/0339090 A1 Nov. 20, 2014

(30) Foreign Application Priority Data

May 17, 2013 (EP) .................................... 13168227

(51) Int. Cl.
*B01L 3/00* (2006.01)
*G01N 27/447* (2006.01)
*G01N 21/65* (2006.01)

(52) U.S. Cl.
CPC ..... *B01L 3/50273* (2013.01); *B01L 3/502738* (2013.01); *B01L 3/502746* (2013.01);
(Continued)

(58) Field of Classification Search
CPC ..... B01L 2300/0636; B01L 2300/0829; B01L 2300/168; B01L 2400/0406;
(Continued)

(56) References Cited

U.S. PATENT DOCUMENTS 5,800,690 A * 9/1998 Chow .............. G01N 27/44713
204/451
2004/0231987 A1* 11/2004 Sterling .............. B01L 3/50273
204/450

(Continued)

OTHER PUBLICATIONS

Cho, SK, Moon, H, Kim, CJ; Creating, transporting, cutting, and merging liquid droplets by electrowetting-based actuation of digital microfluidic circuits; Journal of Microelectromechanical systems; vol. 12, issue 1; p. 70-80; published Feb. 2003.*

(Continued)

*Primary Examiner* — Sean E Conley
*Assistant Examiner* — Benjamin R Whatley
(74) *Attorney, Agent, or Firm* — McDonnell Boehnen Hulbert & Berghoff LLP

(57) ABSTRACT

An example micro-fluidic device includes a micro-fluidic channel having an inner surface and a plurality of pillars positioned along the inner surface. The device further includes a plurality of power supplies connected to the pillars. Another example micro-fluidic device includes a micro-fluidic channel having an inner surface and a plurality of pillars positioned along the inner surface. The device further includes a power supply. The pillars are grouped into at least two groups of pillars, each group of pillars including at least two pillars, and all pillars of at least one group of pillars are connected to the power supply. In another example, a sensing system for detecting bioparticles includes a micro-fluidic device, wherein a surface of each pillar comprises functionalized plasmonic nanoparticles or functionalized SERS nanoparticles, a radiation source for radiating the micro-fluidic device, and a detector for detecting SERS signals or surface plasmon resonance.

18 Claims, 12 Drawing Sheets

(52) U.S. Cl.
CPC ..... *G01N 21/658* (2013.01); *G01N 27/44704* (2013.01); *B01L 2300/0636* (2013.01); *B01L 2300/0829* (2013.01); *B01L 2300/168* (2013.01); *B01L 2400/0406* (2013.01); *B01L 2400/0427* (2013.01); *B01L 2400/0688* (2013.01); *B01L 2400/086* (2013.01)

(58) Field of Classification Search
CPC ..... B01L 2400/0427; B01L 2400/0688; B01L 2400/086; B01L 3/50273; B01L 3/502738; B01L 3/502746; G01N 27/44704
See application file for complete search history.

(56) References Cited

U.S. PATENT DOCUMENTS

| | | | |
|---|---|---|---|
| 2007/0059488 A1* | 3/2007 | Aizenberg | B01L 3/502746 428/141 |
| 2011/0247938 A1* | 10/2011 | Wang | B01L 3/502792 204/603 |
| 2011/0266151 A1* | 11/2011 | Jansson | B01L 3/502707 204/451 |
| 2013/0146459 A1* | 6/2013 | Bazant | B01F 13/0071 204/454 |
| 2014/0154703 A1* | 6/2014 | Skelley | B01L 3/502761 435/7.23 |
| 2014/0374621 A1* | 12/2014 | Chou | G01N 21/6452 250/453.11 |
| 2014/0378339 A1* | 12/2014 | Lammertyn | B01L 3/502707 506/9 |

OTHER PUBLICATIONS

Jacobson, SC, Ermakov, SV, Ramsey, MJ; "Minimizing the number of voltage sources and fluid reservoirs for electrokinetic valving in microfluidic devices"; Analytical Chemistry, vol. 71, issue 15; p. 3273-3276; published Aug. 1, 1999.*

* cited by examiner

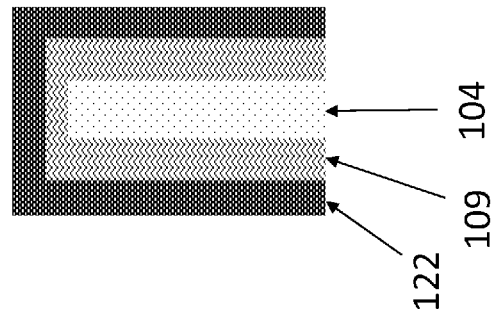
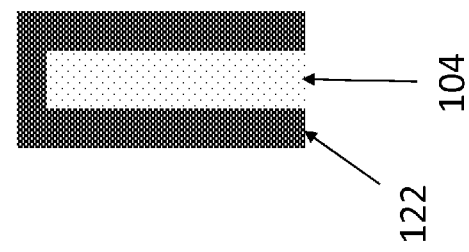
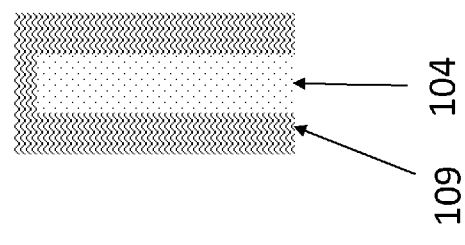

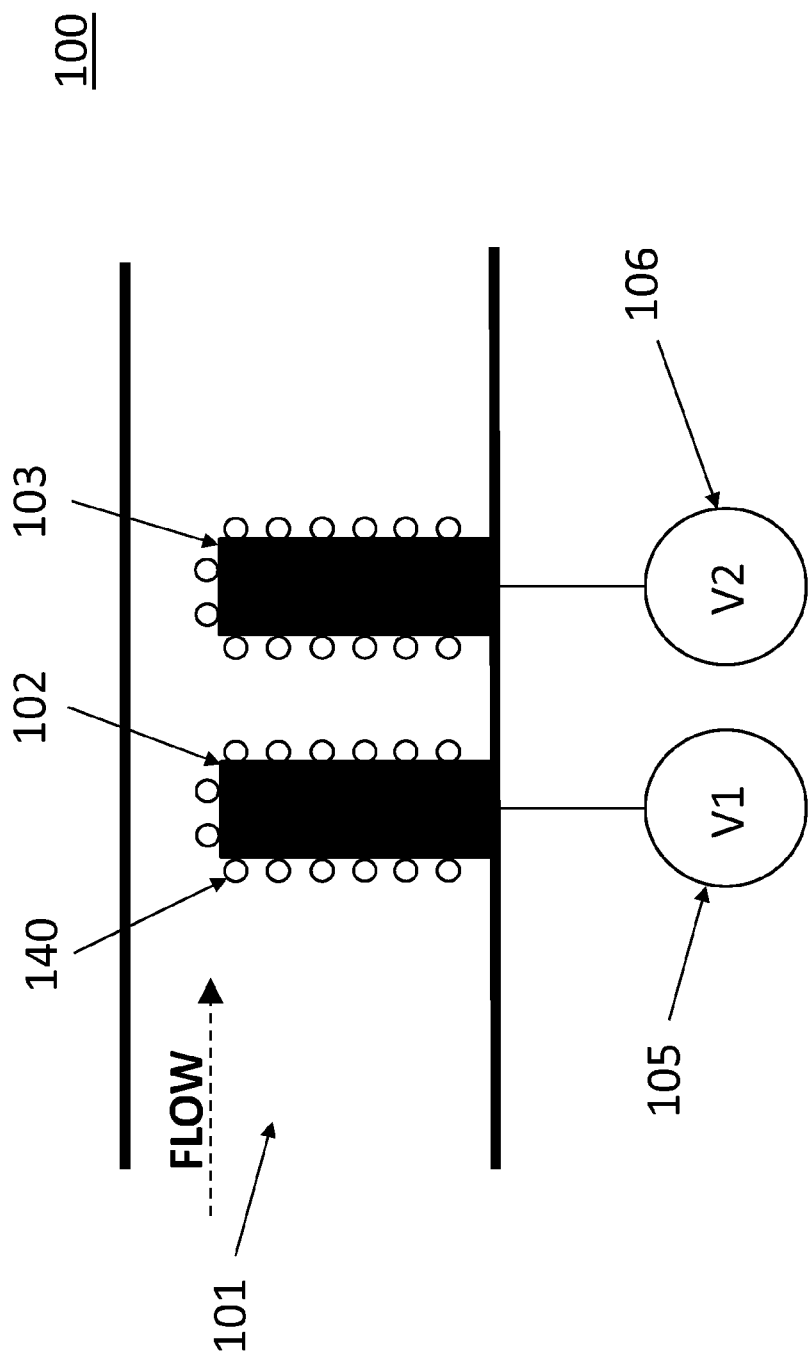

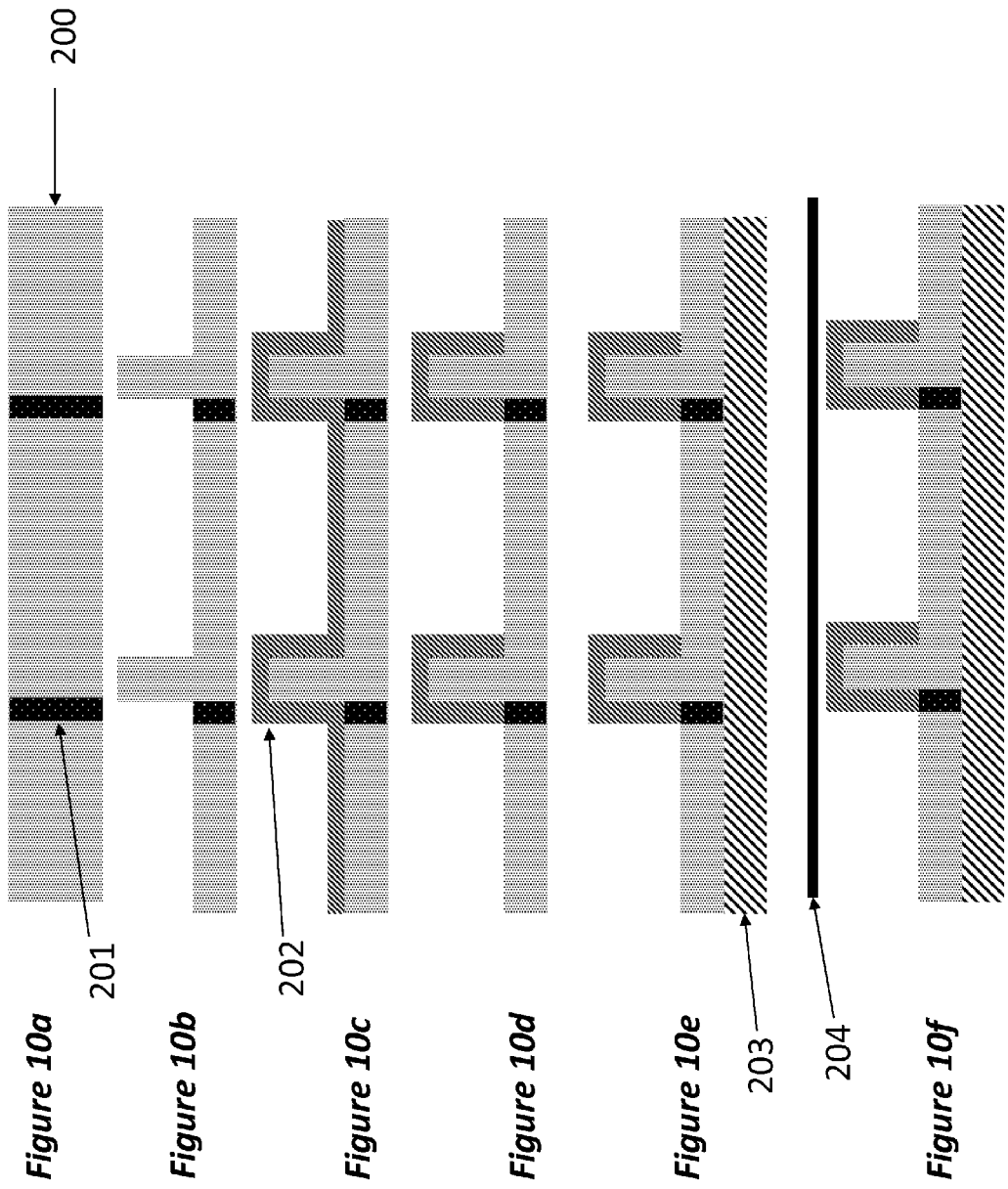

ELECTRIC CONTROLLED MICRO-FLUIDIC DEVICE

CROSS-REFERENCE TO RELATED APPLICATION

This application claims priority to European Patent Application No. 13168227.0 filed on May 17, 2013, the contents of which are hereby incorporated by reference

BACKGROUND

This disclosure is related to the field of micro-fluidic devices. In particular, the disclosure is related to capillary flow micro-fluidic devices or lateral flow micro-fluidic devices.

Capillary flow devices can be used to detect the presence or the absence of an analyte in a fluid sample. An advantage of these devices is that no external pumps or valves are necessary to pump the fluid through the device. Inside these capillary flow devices, a capillary action is created to ensure that the fluid flows through the device.

In state of the art capillary flow devices, a fluid propagates through the device in one direction. Also, in state of the art capillary flow devices, a fluid can only propagate continuously through the device, e.g., it cannot be stopped. This is a disadvantage as this limits the functionality of the device for liquid manipulation that makes these devices only suitable for "one-step" bio-assays. The unidirectional fluid movement highly limits the application of these devices, as most of the bioassays require multiple steps whereby, for example, first, a binding with the analyte takes place and, second, a detection is performed. Another disadvantage is the flow resistance a fluid experiences inside state of the art capillary flow devices. When the fluid propagates through the device, the fluid movement tends to slow down and eventually stop as the flow resistance increases along the channel of the device.

There is a desire for capillary flow devices that overcome one or more disadvantages of the prior art, in particular, in which the propagation of the fluid through the capillary flow device can be more precisely controlled.

SUMMARY

One feature of the disclosure relates to electrically controlling the capillary flow in a micro-fluidic device. The electrical control can be achieved via electrically modifying a surface charge of capillary micro-fluidic channels.

In a first aspect of the disclosure, a micro-fluidic device includes a micro-fluidic channel having an inner surface, a plurality of pillars positioned along a length of the inner surface of the micro-fluidic channel. The plurality of pillars being configured for creating a capillary action in the micro-fluidic channel when a fluid is present in the micro-fluidic channel. The device may also include a plurality of electric power supplies, and each electric power supply may be suitable for generating a different voltage. Further, each pillar may be connected to a different electric power supply.

According to an embodiment of the disclosure, each pillar may include a conductive core connected to a respective electric power supply. According to an embodiment of the disclosure, each pillar may be fabricated from a conductive material, such as doped Silicon or carbon. According to an embodiment of the disclosure, each pillar may be fabricated from a plasmonic material, such as gold or silver.

According to an embodiment of the disclosure, a dielectric layer may cover a surface of the conductive core.

According to an embodiment of the disclosure, the surface of the conductive core or a surface of the dielectric layer may be covered with a hydrophobic layer.

According to an embodiment of the disclosure, each pillar may include a core, and a surface of the core may be covered with a metal layer that is connected to an electric power supply.

According to an embodiment of the disclosure, a surface of the metal layer may be covered with a dielectric layer.

According to an embodiment of the disclosure, a surface of the dielectric layer may be covered with a hydrophobic layer.

According to an embodiment of the disclosure, a selector may connect each pillar to its respective electric power supply.

According to an embodiment of the disclosure, the selector may include at least one transistor.

According to an embodiment of the disclosure, each pillar may further be connected to biosensing circuitry for sensing an electrochemical signal. This electrochemical signal may result from an interaction between a bioparticle and a receptor molecule present on a pillar, for example.

According to an embodiment of the disclosure, the inner surface of the micro-fluidic channel may include first and second regions that include pillars and a third region in between the first and second regions that may not include pillars. Further, a first surface of the third region may include a hydrophobic layer and a second surface of the third region, which opposes the first surface, may include hydrophilic layer.

According to an embodiment of the disclosure, each electric power supply may be configured to generate a pulsed electric voltage.

In a second aspect of the disclosure, a micro-fluidic device includes a micro-fluidic channel having an inner surface and a plurality of pillars positioned along the inner surface of the micro-fluidic channel. The pillars may be configured for creating a capillary action in the micro-fluidic channel. The device also may include at least one electric power supply. Further, the plurality of pillars may be grouped into at least two groups of pillars and each group of pillars may include at least two pillars. In one example, all the pillars of at least one group of pillars are connected to the at least one power supply.

According to an embodiment of the disclosure, a surface of each pillar may include plasmonic nanoparticles or SERS nanoparticles.

According to embodiments of the disclosure, the nanoparticles may be functionalized with receptor molecules to bind target bioparticles.

According to embodiments of the disclosure, some or all of the pillars may be plasmonic pillars fabricated from a plasmonic material, such as gold or silver. The plasmonic pillars may be functionalized with receptor molecules to bind target bioparticles.

In a third aspect of the disclosure, a sensing system for detecting bioparticles includes a micro-fluidic device according to any embodiment or aspect of the disclosure, a radiation source for radiating the micro-fluidic device, and a detector for detecting SERS signals or surface plasmon resonance from the micro-fluidic device.

BRIEF DESCRIPTION OF THE DRAWINGS

FIGS. 3a-g illustrate different embodiments of pillars.

FIG. 6 illustrates a micro-fluidic device according to an embodiment of the disclosure including pillars having particles.

FIGS. 10a-f illustrate a method of fabricating a micro-fluidic device according to an embodiment of the disclosure.

DETAILED DESCRIPTION OF THE DISCLOSURE

Figure 1:
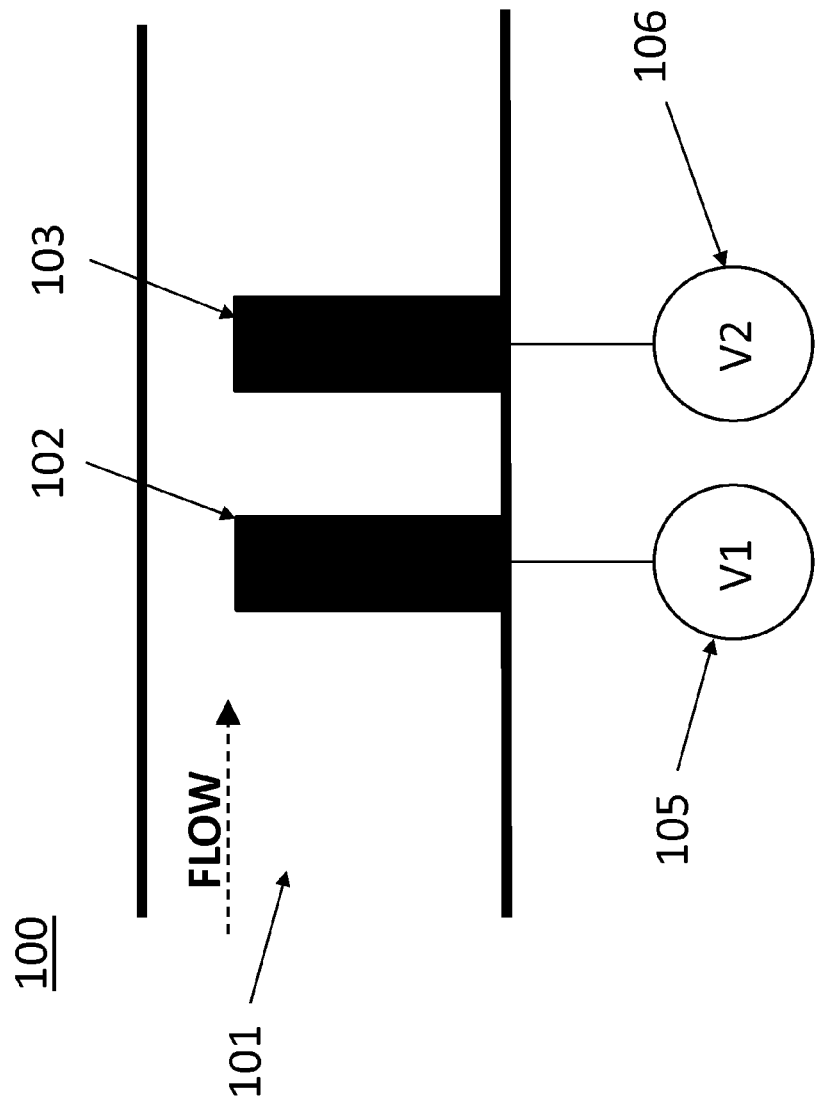
FIG. 1 illustrates a micro-fluidic device according to an embodiment of the disclosure.

Where in embodiments of the present disclosure reference is made to "electrowetting" or "electrowetting behavior," this is defined generally as the modification of wetting properties of a surface with an applied electric field.

Where in embodiments of the present disclosure reference is made to "a bioparticle," this is defined generally as a relatively small or the smallest discrete portion or amount of biological material. This encompasses, e.g., a cell or a molecule.

Where reference is made to "target bioparticles," these are specific types of particles that are targeted for detection.

Where in embodiments of the present disclose reference is made to body fluids, this is defined as liquids originating from inside the bodies of humans or animals, which includes fluids that are excreted or secreted from the body, as well as body water.

Where in embodiments of the present disclose reference is made to Surface Enhanced Raman Spectroscopy (SERS), this is a very sensitive technique to measure small molecules, even at the single molecule level. It is a surface sensitive technique that results in the enhancement of Raman scattering by molecules adsorbed or bound (in close contact/in the vicinity of) on metal surfaces.

In this disclosure, it is described how the modification of wetting properties of surfaces (known as electrowetting) in capillary micro-fluidic devices can be used to control the propagation of a fluid in these devices.

Wetting is the ability of a liquid to maintain contact with a solid surface, resulting from intermolecular interactions when the two are brought together. The degree of wetting (wettability) is determined by a force balance between adhesive and cohesive forces. The contact angle is the angle at which the liquid-vapor interface meets the solid-liquid interface. The electrowetting effect has been defined as the change in solid-electrolyte contact angle due to an applied potential difference between the solid and the electrolyte.

The phenomenon of electrowetting can be understood in terms of the forces that result from the applied electric field. The fringing field at the corners of an electrolyte droplet tend to pull the droplet down onto the electrode, lowering the macroscopic contact angle and increasing the droplet contact area.

In various embodiments, the micro-fluidic channel of the micro-fluidic devices presented in this disclosure includes pillars, which are configured to create a capillary action in the micro-fluidic channel. The pillars may include an array of pillars inside the micro-fluidic channel. The array of pillars may be configured to create a capillary action in the micro-fluidic channel. The surface properties of the pillars (e.g., a roughness, a composition, and the like), the number of pillars, an aspect ratio of the pillars, and a distance between the pillars in an array of pillars is determined to create the capillary action. The pillars may be micro-pillars or nano-pillars, for example.

In a first aspect of the disclosure, a micro-fluidic device is presented, wherein the wetting properties of a surface of each pillar in the micro-fluidic channel can be modified electrically to control the propagation of a fluid in the micro-fluidic channel. The ability to change the wetting properties of the surface of each pillar implies that each pillar individually may be connected to an individual power supply. By controlling the voltage supplied to each pillar individually, the wetting properties for each pillar can be modified. By modifying the wetting properties of each pillar individually, a gradually increasing or decreasing pressure gradient may be created along the micro-fluidic channel when a fluid is present in the micro-fluidic channel. Prior art capillary flow micro-fluidic systems may suffer from flow resistance in the micro-fluidic channel. The pressure gradient (e.g., increasing or decreasing) that is created in the micro-fluidic channel can overcome this flow resistance. Further, the pressure created in the device can also be used to stop or change the direction of the propagation of a fluid in the micro-fluidic channel.

In a second aspect of the disclosure, a micro-fluidic device is presented, of which the wetting properties of the surface of a group of pillars in the micro-fluidic channel can be modified to control the propagation of a fluid in the micro-fluidic channel. By modifying the wetting properties of a group of pillars in the micro-fluidic channel, the propagation of a fluid in the micro-fluidic channel can, for example, be focused to a specific part in the micro-fluidic channel, such as to the part of the micro-fluidic channel comprising pillars of which the wetting properties of the surface have been modified (e.g., those pillars of which the contact angle with the fluid has been decreased). Also, by simultaneously controlling the wetting properties of a group of pillars in the micro-fluidic channel, the propagation of a fluid in the micro-fluidic channel may be stopped or blocked, for example.

In a third aspect of the disclosure, a micro-fluidic system for detecting bioparticles is presented. The system includes a micro-fluidic device as disclosed herein. Nanoparticles may be positioned on the pillars present in the micro-fluidic channel. The nanoparticles may be used to attach bioparticles. For this purpose, the nanoparticles may include a surface chemistry to attract the bioparticles of interest. Alternatively, the pillars may be fabricated from a plasmonic material (e.g., gold or silver) and functionalized. In this case, nanoparticles do not need to be attached to the pillars. A radiation source may be used to radiate the micro-fluidic system. A detector may be used to perform the detection of the bioparticles. The detection of bioparticles may be done using surface plasmon resonance or SERS techniques, for example. Accordingly, the selection of the type of the particles on the pillars may depend on the chosen detection technique, e.g., plasmon nanoparticles or SERS particles.

A detailed description of the different aspects of this disclosure is described below.

In a first aspect of the disclosure, a micro-fluidic device 100 is presented. The device includes a micro-fluidic channel 101 having an inner surface and a plurality of pillars 102, 103 positioned along a length of the inner surface of the micro-fluidic channel 101. The pillars 102, 103 are configured for creating a capillary action in the micro-fluidic channel 101 when a fluid is present in the micro-fluidic channel. The device 100 also includes a plurality of electric power supplies 105, 106. Each electric power supply 105, 106 is suitable for generating a different voltage, and each pillar 102, 103 is connected to a different electric power supply 105, 106 pillars.

The micro-fluidic device 100 is a capillary flow device in which the propagation of a fluid sample inside the micro-fluidic channel 101 can be controlled using electrowetting. The fluid sample may be a body fluid sample such as blood, for example. The fluid sample may be a water based fluid. The fluid sample may also be an electrolyte.

Figure 2:
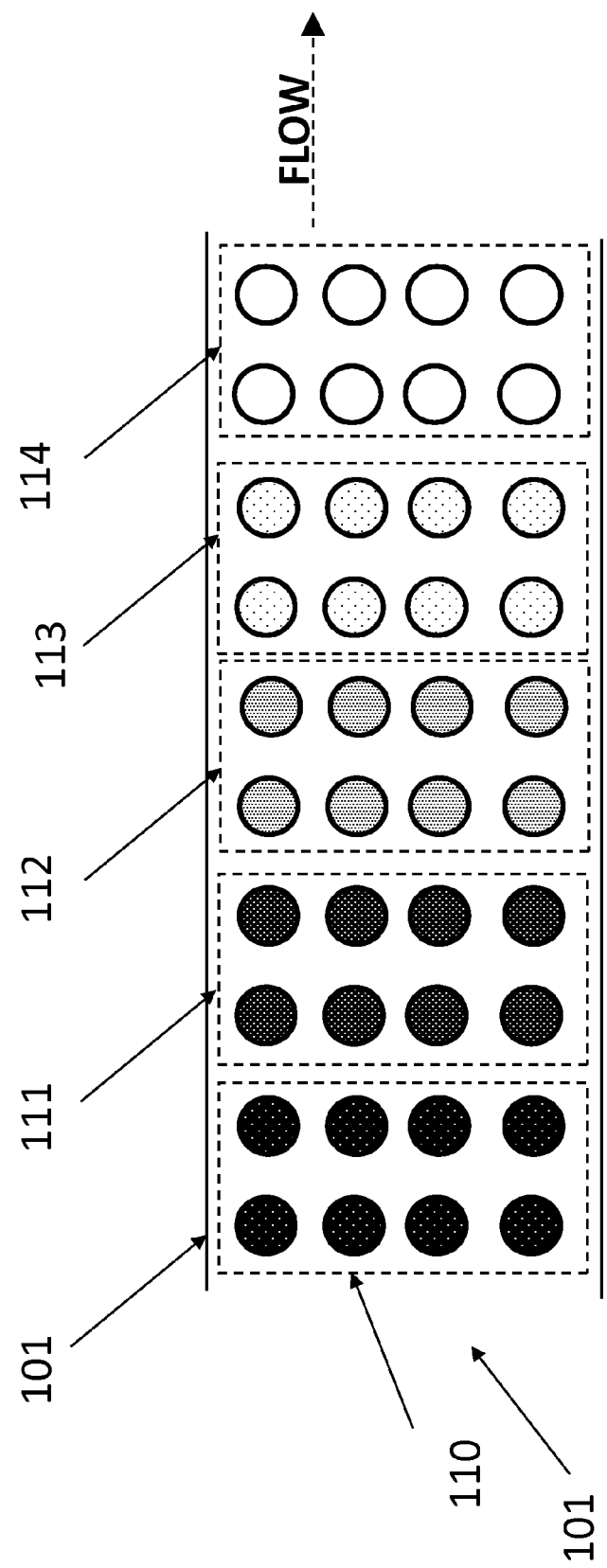
FIG. 2 illustrates a micro-fluidic device according to an embodiment of the disclosure with different electrowetting behavior along a channel.

A device 100 according to the first aspect of the disclosure is illustrated in FIG. 1. The device includes a micro-fluidic channel 101 with a plurality of pillars 102, 103. Each pillar 102, 103 is individually connected to a different electric power supply 105, 106. The plurality of pillars 102, 103 are configured to enable a capillary flow inside the micro-fluidic channel 101. By controlling or changing the electrical voltage that is applied to each pillar 102, 103, the wetting properties (electrowetting behaviour) of each pillar 102, 103 can be changed individually. As the propagation of a fluid in a capillary device 100 is determined by the wettability of the device 100, the pressure (gradient) in the device 100 can be changed by varying the electrowetting behaviour of each pillar 102, 103. As the pressure in the device 100 can be changed, e.g., along the length of the micro-fluidic channel 101, a flow resistance that increases along the micro-fluidic channel 101 can be overcome. As the electrical voltage for each pillar can be controlled, the direction of the propagation of a fluid can be controlled by changing the pressure gradient in the micro-fluidic channel 101. This is illustrated in FIG. 2. Each group of pillars 110, 111, 112, 113, 114 is connected to a different power supply. As the wettability of the pillars depends on the electric voltage connected to the pillars, a pressure gradient that increases or decreases along the micro-fluidic channel 101 may be created. The electric voltage may be a DC voltage.

According to an embodiment of the disclosure, the pillars may be micro-pillars or nano-pillars. According to embodiments of the disclosure, the diameter of the pillars may vary from 1 nm to 1 mm. The aspect ratio of the pillars (e.g., height of the pillar divided by the diameter of the pillar) may vary from 0.1 to 100. According to a specific embodiment, the height of a pillar is 25 um, the diameter of a pillar is 2 um, and the distance between pillars is 1 um. In another embodiment, the height of a pillar is 25 um, the diameter of a pillar is 5 um, and the distance between pillars is 2.5 um. In another embodiment the height of a pillar is 25 um, the diameter of a pillar is 2.5 um, and the distance between pillars is 1.25 um.

According to an embodiment of the disclosure, a plurality of electric power supplies are connected to a plurality of pillars and the electric voltage of each pillar may be controlled individually by an electric power supply.

According to another embodiment of the disclosure, the micro-fluidic device as presented in the first aspect of the disclosure may include an electric power supply and additional circuitry connected to the electric power supply suitable for providing a different voltage to each pillar. The additional circuitry may be a power distribution network suitable for providing a different voltage to each pillar.

FIG. 2 illustrates an embodiment of the disclosure that includes a micro-fluidic device 101 with a plurality of pillars inside the micro-fluidic channel 101. The pillars are located on an inner surface of the micro-fluidic channel 101. The pillars are grouped into five groups of pillars 110, 111, 112, 113, 114. Each group of pillars 110, 111, 112, 113, 114 is connected to a different power supply. The electric voltage applied to different groups may differ. This way, the electrowetting behaviour of each group of pillars 110, 111, 112, 113, 114 may be different. This configuration enables decreasing or increasing the contact angle between the pillar and the fluid along the micro-fluidic channel 101, thereby allowing more precise control over the propagation of the fluid in the micro-fluidic channel 101. The electric voltage of each group of pillars 110, 111, 112, 113, 114 may be changed while the fluid flows through the micro-fluidic channel 101. This allows a dynamic control over the propagation of the fluid through the micro-fluidic channel 101. The contact angle between the pillar and the fluid is changed depending on the electric voltage of each pillar. The increase or decrease of the contact angle causes a pressure change in the micro-fluidic device.

According to other embodiments of the disclosure, each pillar may have a different composition. According to an embodiment of the disclosure, each pillar 102, 103 may comprise a conductive core 107 connected to an electric power supply 105, 106. According to an embodiment of the disclosure, a dielectric layer 109 may cover the surface of the conductive core 107. According to an embodiment of the disclosure, the surface of the conductive core 107 or the surface of the dielectric layer 109 may be covered with a hydrophobic layer 122. According to an embodiment of the disclosure, each pillar 102, 103 may comprise a core 107, and wherein the surface of the core 107 may be covered with a metal layer 108 which may be connected to an electric power supply 105, 106. According to an embodiment of the disclosure, the surface of the metal layer 108 may be covered with a dielectric layer 109. According to an embodiment of the disclosure, the surface of the dielectric layer 109 may be covered with a hydrophobic layer 122. Different pillar compositions are illustrated in FIGS. 3a-g.

FIG. 3a illustrates a pillar comprising a conductive core 104. The conductive core 104 may be a gold, silver, copper, or platinum core, for example. The selection of the material of the conductive core 104 may be based on the type of fluid propagating through the micro-fluidic channel 101. When the fluid is an electrolyte, a chemically stable metal may be selected, such as gold or platinum, to avoid corrosion of a metal core by the electrolyte.

FIG. 3b illustrates a pillar comprising a conductive core 104. The conductive core 104 may be a metal core, such as a gold, silver, copper, or platinum core. Alternatively, the conductive core 104 may be fabricated from a conductive material, such as an electrically conductive silicon. In this example, the surface of the conductive core 104 is covered with a dielectric layer 109. The dielectric layer 109 may be fabricated from an isolating material, e.g., silicon nitride such as SiN or silicon oxide such as SiO2. The material of the dielectric layer 109 may be selected in order to have a dual functionality of the dielectric layer 109, for example, 1)

the dielectric layer 109 may function as an isolator between a pillar and a fluid, and 2) the dielectric layer 109 may function as a hydrophobic layer towards the fluid propagating in the channel. In this case, the dielectric layer may be a polydimethylsiloxane (PDMS), polymer or Teflon layer, or another suitable material.

FIG. 3c illustrates a pillar comprising a conductive core 104. The conductive core 104 may be a metal core, such as a gold, silver, copper, or platinum core. Alternatively, the conductive core 104 is a fabricated from a conductive material, such as an electrically conductive silicon. The surface of the conductive core 104 is covered with a hydrophobic layer 122. The hydrophobic layer 122 may be a polymer layer, for example.

FIG. 3d illustrates a pillar comprising a conductive core 104. The conductive core 104 may be a metal core, such as a gold, silver, copper, or platinum core. Alternatively, the conductive core 104 is a fabricated from a conductive material, such as an electrically conductive silicon. The surface of the conductive core 104 is covered with a dielectric layer 109. The dielectric layer 109 may be fabricated from an isolating material, e.g., silicon nitride, such as SiN or silicon oxide, such as SiO2. The surface of the dielectric layer 109 is covered with a hydrophobic layer 122. The hydrophobic layer 122 may be a polymer layer, for example.

Figure 3G:
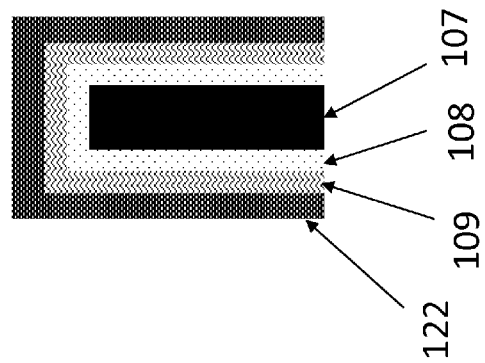
Figure 3F:
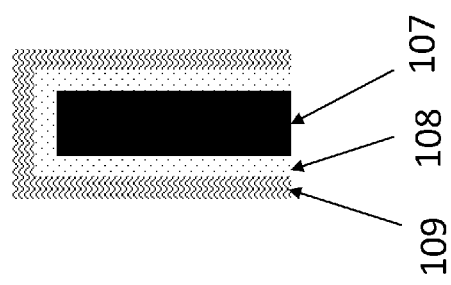
Figure 3E:
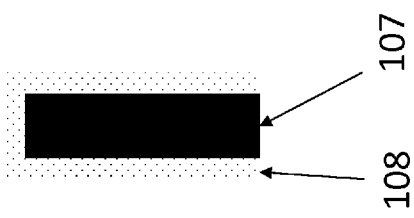

FIG. 3e illustrates a pillar comprising a core 107. The material of the core may be, e.g., silicon or a polymer. The surface of the core 107 is covered with an electrically conductive layer, such as a metal layer 108. The metal layer 108 may be, e.g., a gold, silver, copper, or platinum layer. When a fluid propagating through the micro-fluidic channel is an electrolyte, a chemically stable metal may be selected, such as gold or platinum to avoid corrosion of the metal layer 108 by the electrolyte.

FIG. 3f illustrates a pillar comprising a core 107. The material of the core may be, e.g., silicon or a polymer. The surface of the core 107 is covered with an electrically conductive layer, such as a metal layer 108. The metal layer 108 may be a gold, silver, copper, or platinum layer, for example. The surface of the metal layer 108 is covered with a dielectric layer 109. The dielectric layer 109 may be fabricated from an isolating material, e.g., silicon nitride, such as SiN, or silicon oxide, such as SiO2. The material of the dielectric layer 109 may be selected in order to have a dual functionality of the dielectric layer 109: 1) the dielectric layer 109 may function as an isolator and 2) the dielectric layer 109 may function as a hydrophobic layer. In this case, the dielectric layer may be a Polydimethylsiloxane (PDMS), polymer or Teflon layer, or another suitable material.

FIG. 3g illustrates a pillar comprising a core 107. The material of the core may be, e.g., silicon or a polymer. The surface of the core 107 is covered with an electrically conductive layer, such as a metal layer 108. The metal layer 108 may be a gold, silver, copper, or platinum layer, for example. The surface of the metal layer 108 is covered with a dielectric layer 109. The dielectric layer 109 may be fabricated from an isolating material, e.g., silicon nitride, such as SiN, or silicon oxide, such as SiO2. The surface of the dielectric layer 109 is covered with a hydrophobic layer 122. The hydrophobic layer 122 may be a polymer layer, for example.

The selection of the composition of the pillar depends on the type of fluid propagating through the micro-fluidic channel. When an electrolyte fluid is used, the use of a dielectric layer is not essential. The electrolyte fluid may be in direct contact with a conductive material, such as a metal layer or a conductive core (e.g., a metal core). The use of electrolyte fluids induces the formation of an electrical double layer on top of the conductive core or layer (e.g., metal) when an electric voltage is applied to the conductive core or layer. Due to this physical effect, an additional dielectric layer is not essential.

According to embodiments of the disclosure, an electric power supply is connected to an electrically conductive layer, such as a metal layer 108 of a pillar or a conductive core 104, such as a metal core or a highly conductive silicon (doped) core of a pillar.

The hydrophobic layer 110 may be a polymer layer, for example. The use of a hydrophobic layer 110 ensures a large contact angle between a pillar and a fluid that increases a contact angle range when using electrowetting. The dielectric layer 109 may be a silicon nitride, such as SiN, or silicon oxide, such as SiO2 layer. The metal layer 108 may be a gold, silver, copper, or platinum layer. The selection of the metal is based on the type of fluid that propagates through the micro-fluidic channel. When the fluid is an electrolyte, a chemically stable metal may be selected, such as gold or platinum.

According to an embodiment, the pillars may be plasmonic pillars, such as gold or silver pillars. The plasmonic pillars are suitable for the detection of a target bioparticle present in a fluid sample. Binding of one or more of the target bioparticles to the surface of the plasmonic pillars causes a change in the optical properties, relative to the optical properties of the plasmonic pillars in the absence of a binding. This change may be measured by an optical detector and allows to indicate the presence of one or more binding events. Additionally, the plasmonic pillars may be designed to have immobilized receptor molecules bound to the plasmonic pillars surface, such that a change in an optical property of the plasmonic pillars is detected on binding of one or more target bioparticles present in a fluid sample to one or more of the immobilized receptor molecules present on the plasmonic pillars surfaces. Preferably, an immobilized receptor molecule layer on the plasmonic pillar surfaces is a thin surface chemistry layer. The metals used for the plasmonic pillars are selected on the basis of their surface plasmon properties. The metals used can be a noble metal, an alkali metal, a transition metal, or any metal selected from the group consisting of gold, rhodium, palladium, silver, osmium, iridium, platinum, titanium, aluminum, or any combination thereof.

According to an embodiment of the disclosure, a selector 141 (see FIG. 5) may connect each pillar to its electric power supply 105, 106. The selector may connect each pillar to a different power supply. Generally, the selector allows each pillar to be selected and individually driven by a power supply. This way, each pillar can be selected and the wettability of each pillar can be controlled individually. This allows for programming of the flow speed and/or flow pattern of the fluid in the micro-fluidic channel 101. In contrast to the gradually-decreasing lateral flow rate that occurs in state of the art lateral flow devices, a nearly constant flow rate can be achieved in the device presented in this disclosure. Further, by changing the wettability pattern of the pillars, the propagation pattern of the capillary flow in the device can be changed. The selector may be embedded in the micro-fluidic channel 101. According to an embodiment of the disclosure, the selector may be a transistor such as a CMOS transistor.

According to embodiments of the disclosure, the micro-fluidic device 100 may comprise additional electronic circuitry for individually addressing each pillar. The additional electronic circuitry may be digital blocks, such as multiplexers, read-out logic, or other digital blocks. These digital blocks may be embedded in the micro-fluidic channel.

According to an embodiment of the disclosure, each pillar may be further connected to biosensing circuitry 142 (see FIG. 7*b*) for sensing an electrochemical signal. The micro-fluidic device may further comprise biosensing circuitry for sensing electrochemical signals from bioparticles. The circuitry may be a biosensor suitable for detecting electrochemical signals. The biosensing circuitry may be connected to each pillar. It may be advantageous that the micro-fluidic device 100 is a compact embedded capillary flow biosensing device that is able to 1) control the flow of a fluid in the micro-fluidic channel 101 of the device 100, and 2) to perform sensing of target bioparticles. It may be advantageous that the flow of the fluid in the micro-fluidic channel 101 can be controlled, stopped, or reversed, as this may increase the sensitivity of the sensing functions. As another potential advantage, an additional bio-assay detection mechanism (e.g., optical, fluorescence, etc.) is not needed to perform the sensing. This allows the device to be miniaturized and compact. To detect bioparticles, in a first stage the propagation of the fluid in the micro-fluidic channel can be controlled (e.g., stopped) by applying a voltage to the pillars in the micro-fluidic channel and, thereafter, when the applied voltage to the pillar is switched off (the pillar is at that stage floating) in a second stage electrochemical sensing may be performed using the same pillars. The biosensing circuitry may be embedded in the micro-fluidic channel 101. The bio-sensing circuitry may be further connected to read-out circuitry.

According to embodiments of the disclosure, pillars in the micro-fluidic channel 101 may be grouped. A different electric voltage provided by at least one electric power supply 104 may be applied to each group of pillars. For example, pillars may be grouped into one group of pillars that are connected to the same electric voltage. This way, the group of pillars may function as a micro-fluidic valve wherein the electric voltage level applied to the group of pillars determines the propagation of the fluid in the micro-fluidic channel 101.

According to an embodiment of the disclosure, the micro-fluidic channel may comprise a reference electrode 120. The reference electrode may be connected to ground. The reference electrode 120 may be positioned in the micro-fluidic channel 101.

According to an embodiment of the disclosure, the inner surface of the micro-fluidic channel 101 may comprise a first and second region 125, 126, respectively, comprising pillars, and a third region 130 in between the first and the second regions comprising no pillars. A first surface of the third region 130 may comprise a hydrophobic layer 127, and wherein a second surface of a region opposing the first surface of the third region may comprise a hydrophilic layer 123.

Figure 4A:
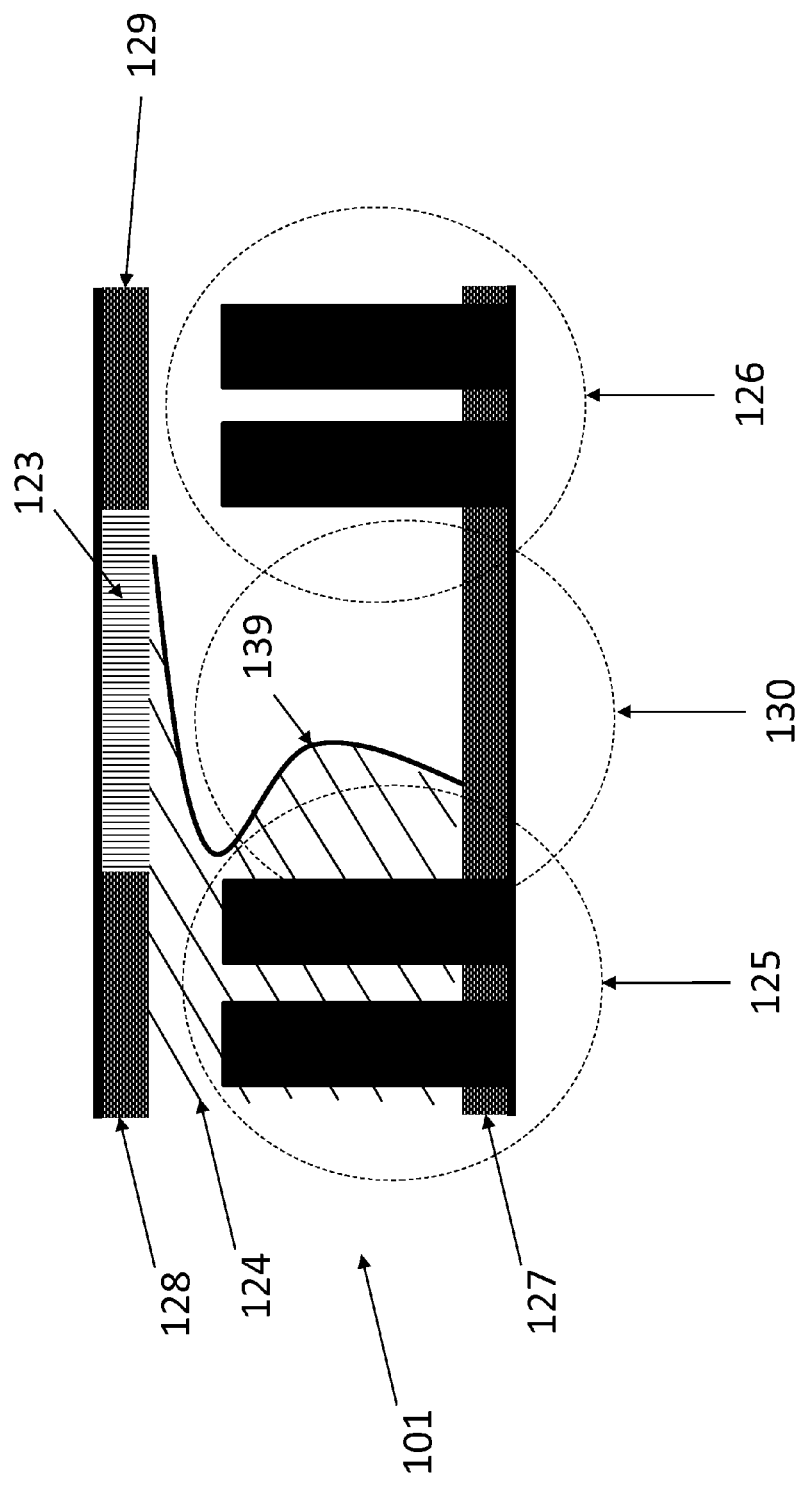
FIG. 4a illustrates a micro-fluidic device according to an embodiment of the disclosure including hydrophobic and hydrophilic layers.

Inner surfaces of the micro-fluidic channel may comprise regions comprising a hydrophobic and/or a hydrophilic layer. Certain parts of the surfaces may comprise a hydrophobic layer while other parts of the surfaces may comprise a hydrophilic layer. This may be advantageous for fluids to bridge gaps between different areas of the micro-fluidic channel comprising pillars as illustrated in FIG. 4*a*, for example. The surface of the micro-fluidic channel comprising pillars may comprise a hydrophobic layer. The hydrophobic layer may also be located in between the pillars.

FIG. 4*a* illustrates an embodiment of the disclosure, in which the micro-fluidic channel 101 comprises two pillar regions 125, 126. In between the first and the second pillar region 125, 126, respectively, there is a third region 130 without pillars. Thus, in the third region 130 there may be capillary action. The surface of the third region 130 comprises a hydrophobic layer 127, and the surface opposite to this surface of the third region 130 comprises a hydrophilic layer 123. The surface opposite to the surface of the first and second region 125, 126 that includes the hydrophobic layer 127 comprises a hydrophobic layer 128, 129, respectively. The contact angle between the hydrophobic layer 127 and the fluid 124 may be large (e.g., larger than 90 degrees). The contact angle between the hydrophilic layer 123 and the fluid 124 is small (e.g., smaller than 90 degrees). This allows a fluid 124 to bridge the third region 130, which comprises no pillars. The fluid profile 139 of the fluid 124 propagating through the micro-fluidic channel 101 shown in FIG. 4 illustrates a large contact angle between the fluid 124 and the hydrophobic layer 127 and a small contact angle between the fluid and the hydrophilic layer 123. This difference in contact angle enables the fluid 124 to propagate through the micro-fluidic channel 101 at locations lacking the presence of pillars in the micro-fluidic channel 101.

Figure 4B:
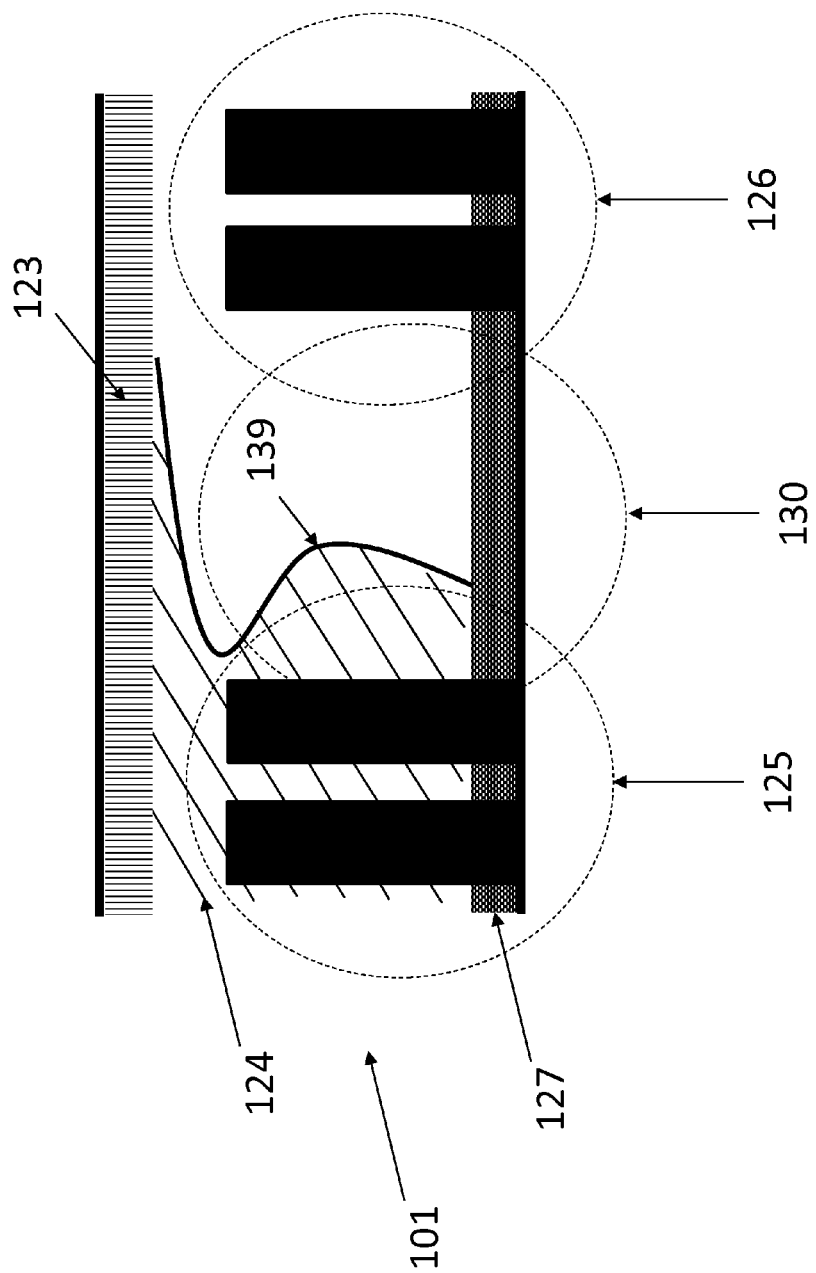
FIG. 4b illustrates a micro-fluidic device according to an embodiment of the disclosure including hydrophobic and hydrophilic layers.

FIG. 4*b* illustrates another embodiment of the disclosure, in which the micro-fluidic channel 101 comprises two pillar regions 125, 126. In between the first and the second pillar region 125, 126, respectively, there is a third region 130 without pillars. Thus, in the third region 130 there may be no capillary action. A first surface of third region 130 comprises a hydrophobic layer 127, and a second surface opposite to the first surface of the first, second, and third regions 125, 126, 130 comprises a hydrophilic layer 123. The contact angle between the hydrophobic layer 127 and the fluid 124 is large. The contact angle between the hydrophilic layer 123 and the fluid 124 is small. This allows a fluid 124 to bridge the third region 130, which comprises no pillars. The fluid profile 139 of the fluid 124 propagating through the micro-fluidic channel 101 shown in FIG. 4 illustrates a large contact angle between the fluid 124 and the hydrophobic layer 127 and a small contact angle between the fluid and the hydrophilic layer 123. This difference in contact angle enables the fluid 124 to propagate through the micro-fluidic channel 101 at locations lacking the presence of pillars in the micro-fluidic channel 101.

Figure 5:
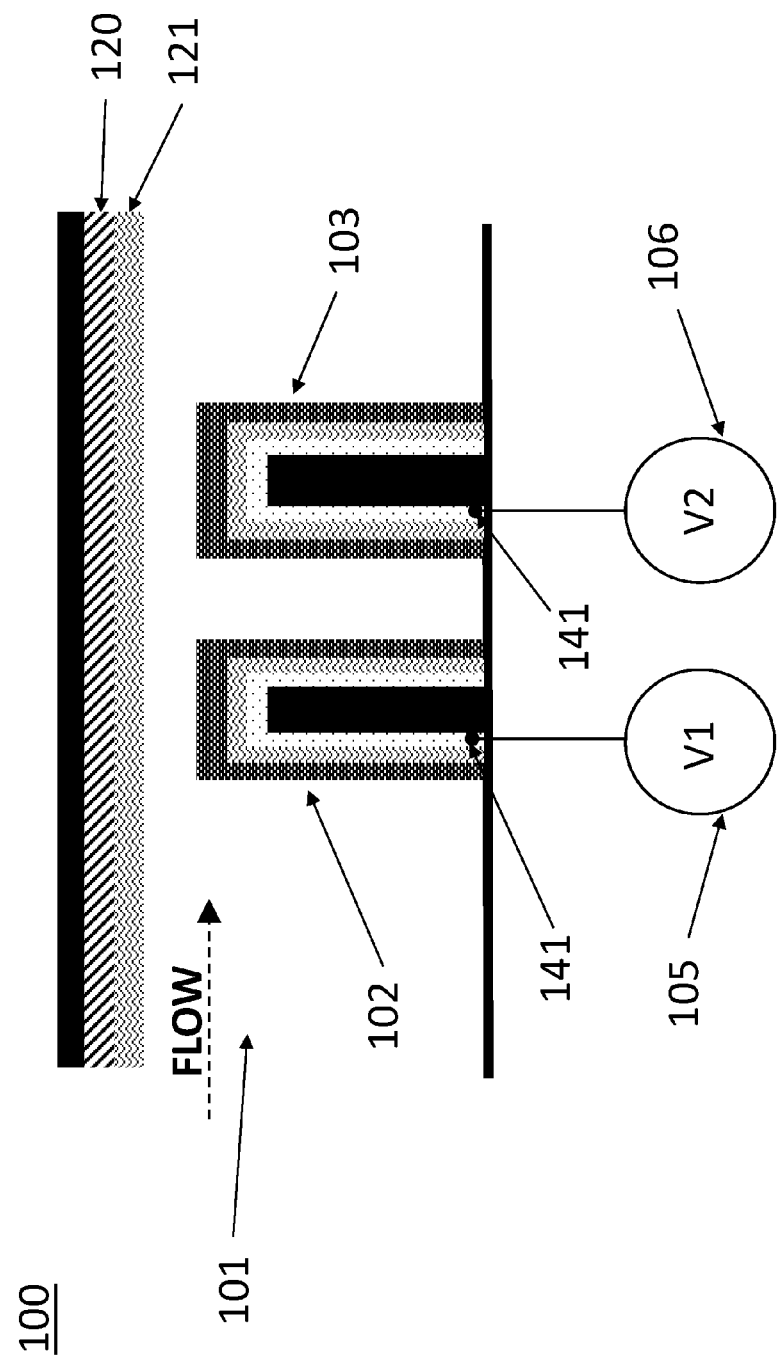
FIG. 5 illustrates a micro-fluidic device according to an embodiment of the disclosure.

FIG. 5 illustrates an embodiment of the disclosure, in which a first surface of the micro-fluidic channel comprises a plurality of pillars 102, 103. Each pillar comprises a core, an electrically conductive layer, a dielectric layer, and a hydrophobic layer. A second surface opposite to the first surface of the micro-fluidic channel 101 comprises a reference electrode 120, and atop the reference electrode 120 a hydrophobic layer 121 is present. The electrically conductive layer of each pillar 102, 103 is connected to a different electric power supply 105, 106.

According to embodiments of the disclosure, other inner surfaces of the micro-fluidic channel 101 may also comprise a hydrophobic or a hydrophobic layer.

According to an embodiment of the disclosure, one or more of the electric power supplies 105, 106 may be configured to generate a pulsed electric voltage, e.g., a pulsed DC voltage. As a potential advantage, by using pulsed signals to control the wettability of different pillars or pillar groups, it is possible to manipulate an individual droplet or droplet groups instead of a continuous flow of fluid.

According to an embodiment of the disclosure, the surface of each pillar comprises plasmonic nanoparticles or SERS nanoparticles.

According to embodiments of the disclosure, the surface of the pillars of the micro-fluidic device may comprise particles 140 such as nanoparticles. The nanoparticles may be nano-spheres, nano-rods, branched nanoparticles, nano-core-shell structures, or other nano-scale objectives with other shapes. FIG. 6 illustrates a micro-fluidic device 100 with pillars 102, 103 comprising particles 140 at the surface of the pillars 102, 103.

According to an embodiment, the nanoparticles may be plasmonic particles. The plasmonic nanoparticles are suitable for the detection of a target bioparticle present in a fluid sample. Binding of one or more of the target bioparticles to the surface of the plasmonic nanoparticles causes a change in the optical properties, relative to the optical properties of the plasmonic nanoparticle in the absence of a binding. This change may be measured by an optical detector and allows the device to indicate the presence of one or more binding events. Additionally, the plasmonic nanoparticles may be designed to have immobilized receptor molecules bound to the plasmonic nanoparticles surface such that a change in an optical property of the plasmonic particles is detected on binding of one or more target bioparticles present in a fluid sample to one or more of the immobilized receptor molecules present on the plasmonic nanoparticle surfaces. The metals used in the plasmonic nanoparticles are selected on the basis of their surface plasmon properties. The metals used can be a noble metal, an alkali metal, a transition metal, or any metal selected from the group consisting of gold, rhodium, palladium, silver, osmium, iridium, platinum, titanium, aluminum, or any combination thereof. The plasmonic nanoparticles can also comprise multiple metals.

According to an embodiment, the nanoparticles may be Surface Enhanced Raman Spectroscopy (SERS) nanoparticles. SERS is a very sensitive technique able to measure small molecules at the single molecule level. It is a surface sensitive technique that results in the enhancement of Raman scattering by molecules adsorbed or bound (in close contact/in the vicinity of) on metal surfaces. Generally, these molecules are adsorbed on or bound to the metal surface. The enhanced Raman scattering may be used to detect a target bioparticle present in a fluid sample. Binding of one or more of the target bioparticles to the surface of the SERS nanoparticles gives rise to an increased Raman signal (SERS signal) when the SERS nanoparticles are being illuminated with a light source. The SERS signal may be measured by a SERS detector and allows the device to indicate the presence of one or more binding events. Additionally, the SERS nanoparticles may be designed to have immobilized receptor molecules bound to the SERS nanoparticle surface such that a SERS signal is detected on binding of one or more target bioparticles present in a fluid sample to one or more of the immobilized receptor molecules present on the SERS nanoparticles surfaces. The SERS particles may be gold (Au), silver (Si), or copper (Cu) nanoparticles or any other metal structure that enables Raman scattering enhancement.

As described herein, it may be advantageous that the flow of the fluid in the micro-fluidic channel 101 can be controlled, stopped, or reversed. As the flow of the fluid in the micro-fluidic channel 101 can be stopped, this allows target bioparticles to bind to the particles or plasmonic pillars, which results in more sensitive SERS or plasmonic resonance measurements. Further, the pillars have a dual functionality as 1) they may provide a capillary action in the micro-fluidic channel and 2) the particles 140 on the pillars or the plasmonic pillars can be used for sensing purposes using SERS (Surface enhanced Raman spectroscopy) or LSPR (localized surface plasmon resonance). The dual functionality of the device increases the compactness of the device as both functionalities can be implemented in the same area. It is potentially a further advantage that by depositing particles 140 on pillars or when using plasmonic pillars, the sensing area is greatly enlarged (surface area enhancement) compared to a flat surface, which results in more sensitive measurements.

According to an embodiment of the disclosure, the micro-fluidic channel 101 may be fully or partly embedded in a semiconductor substrate, such as a silicon substrate.

In a second aspect of the disclosure, a micro-fluidic device includes a micro-fluidic channel 101 having an inner surface, a plurality of pillars 102, 103 positioned along the inner surface of the micro-fluidic channel 101. The pillars 102, 103 are configured for creating a capillary action in the micro-fluidic channel 101. The device also includes at least one electric power supply 105, 106. Further, the plurality of pillars 102, 103 may be grouped into at least two groups 115, 116 of pillars, and each group of pillars may comprising at least two pillars. In one example, all pillars of at least one group of pillars 115 are connected to the at least one power supply 105, 106.

The micro-fluidic device may be used for controlling the propagation of a fluid in a micro-fluidic channel. The device comprises a micro-fluidic channel 101 with a plurality of pillars inside the micro-fluidic channel. The pillars are configured to create a capillary action in the micro-fluidic channel 101 along the length of the channel. The plurality of pillars may be grouped into at least two groups of pillars, and each group of pillars may comprise at least two pillars. The micro-fluidic channel 101 comprises at least one group of pillars of which all pillars are connected to the same power supply. Pillars of another group of pillars may be connected to another power supply. By changing the electric voltage applied to each group of pillars, the propagation of the fluid inside the micro-fluidic channel 101 may be controlled.

Figure 7A:
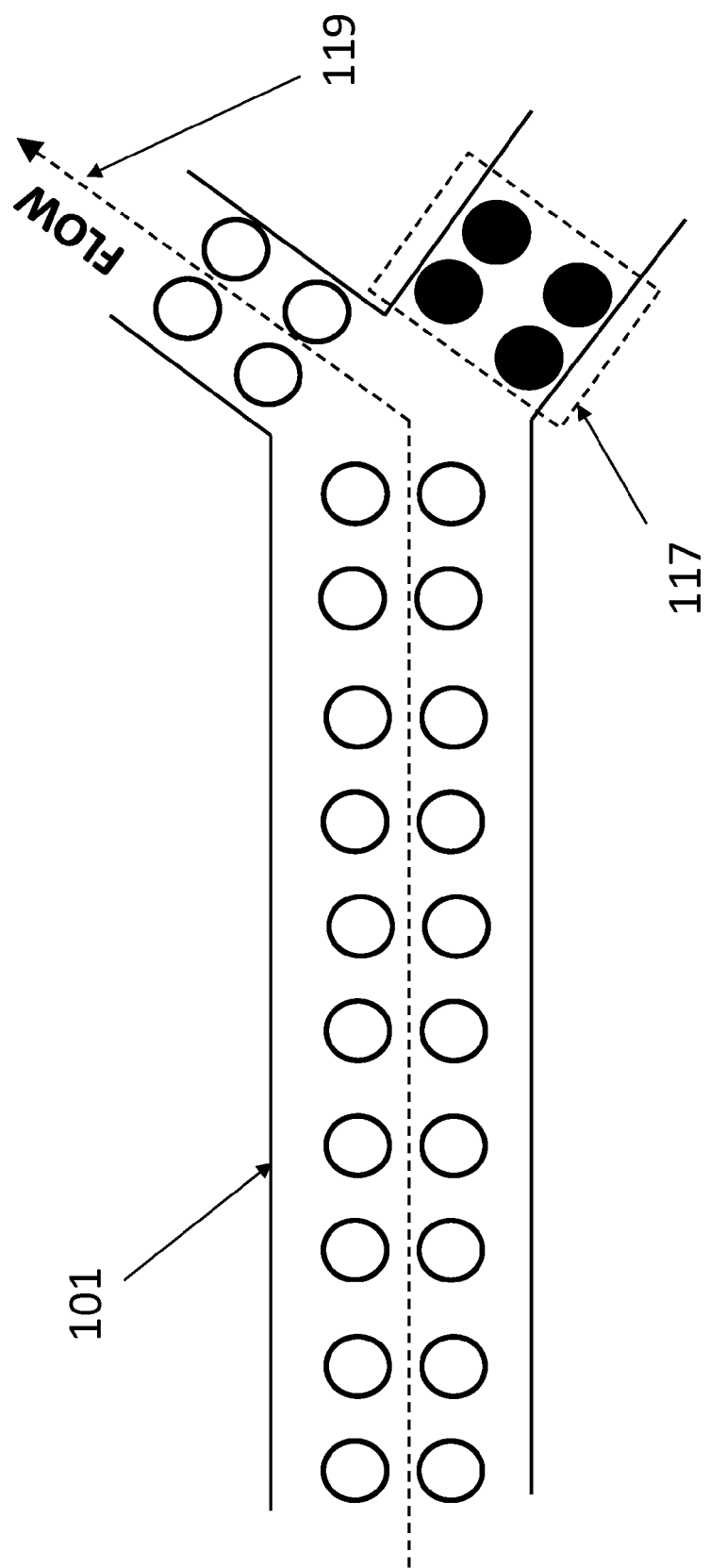
FIG. 7a illustrates a micro-fluidic device according to an embodiment of the disclosure, wherein a group of pillars is configured to operate as an electric valve.
Figure 7B:
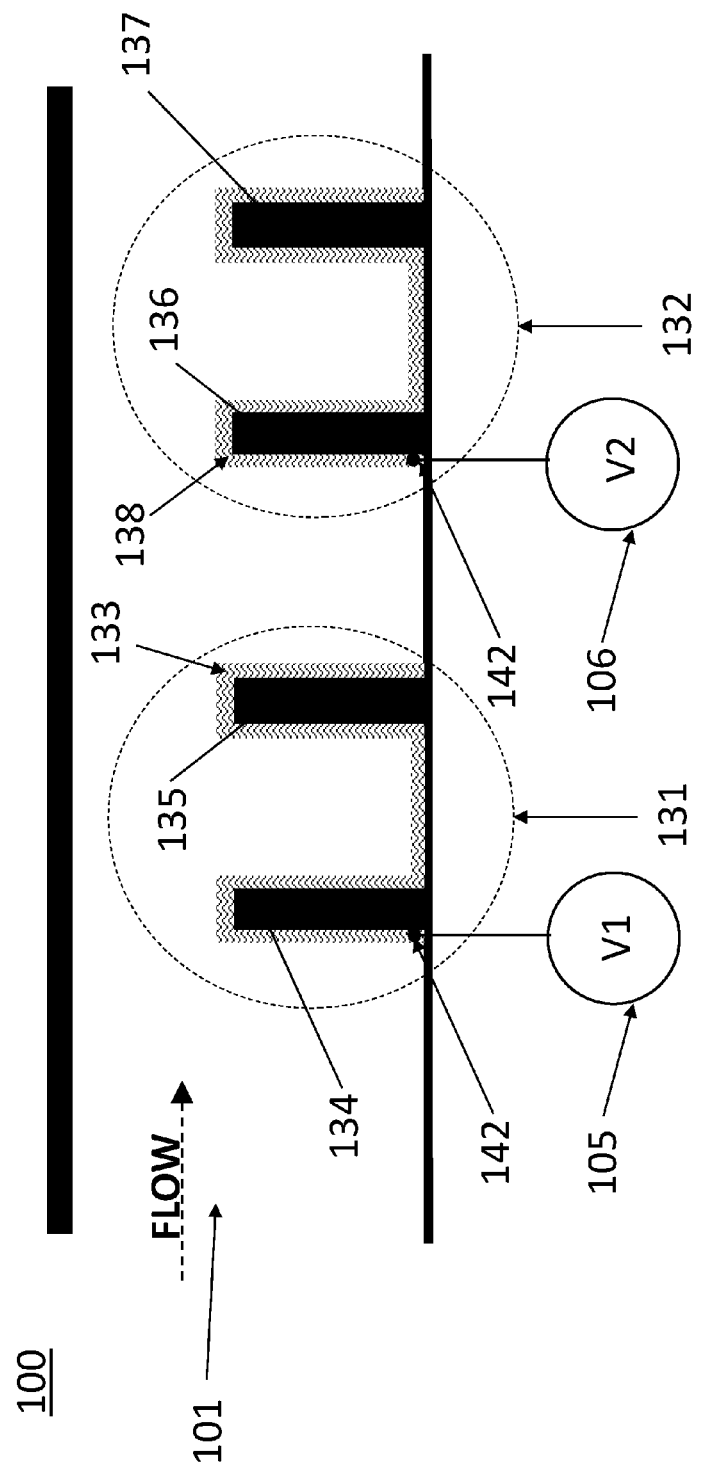
FIG. 7b illustrates a micro-fluidic device according to an embodiment of the disclosure.

FIG. 7b illustrates an embodiment of the disclosure. The micro-fluidic device 101 comprises two groups of pillars 131, 132. Each group comprises two pillars 134, 135, 136, 137. Each group of pillars is covered with a separate metal layer 133, 138. The metal layer 133, 138 of each group of pillars may connected to a different power supply 105, 106, respectively.

Figure 9:
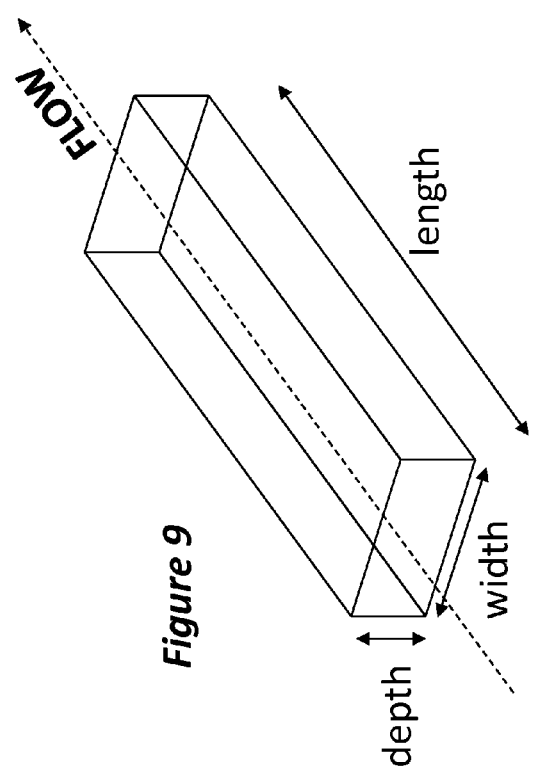
FIG. 9 illustrates the dimensions of a micro-fluidic device in accordance with an embodiment of the disclosure.

When a group of pillars is positioned over the full width ("width" being defined as illustrated in FIG. 9) of the micro-fluidic channel 101, the flow of the fluid in the micro-fluidic channel can be stopped/blocked by de-activating the electrowetting behaviour of these pillars by switching off or lowering the applied voltage to the group of pillars. The group of pillars functions as a micro-fluidic valve. This is illustrated in FIG. 7a.

FIG. 7a illustrates an embodiment of the disclosure. The micro-fluidic device 101 comprises a plurality of pillars. The voltage that is applied to the group of pillars 117 may be changed to allow or block a flow of fluid inside the micro-fluidic channel 101. The group of pillars 117 functions as an electric or micro-fluidic valve. As illustrated in the FIG. 7a, the flow of the fluid in the micro-fluidic device 100 is indicated by arrow 119.

When a group of pillars connected to a power supply is positioned along the micro-fluidic channel 101, a fluid in the micro-fluidic channel 101 can be controlled to propagate in a specific region of the micro-fluidic channel 101, e.g., in a region comprising pillars of which the contact angle between the pillars and the fluid is smaller than the contact angle between the fluid and pillars of another region. This is illustrated in FIG. 8.

Figure 8:
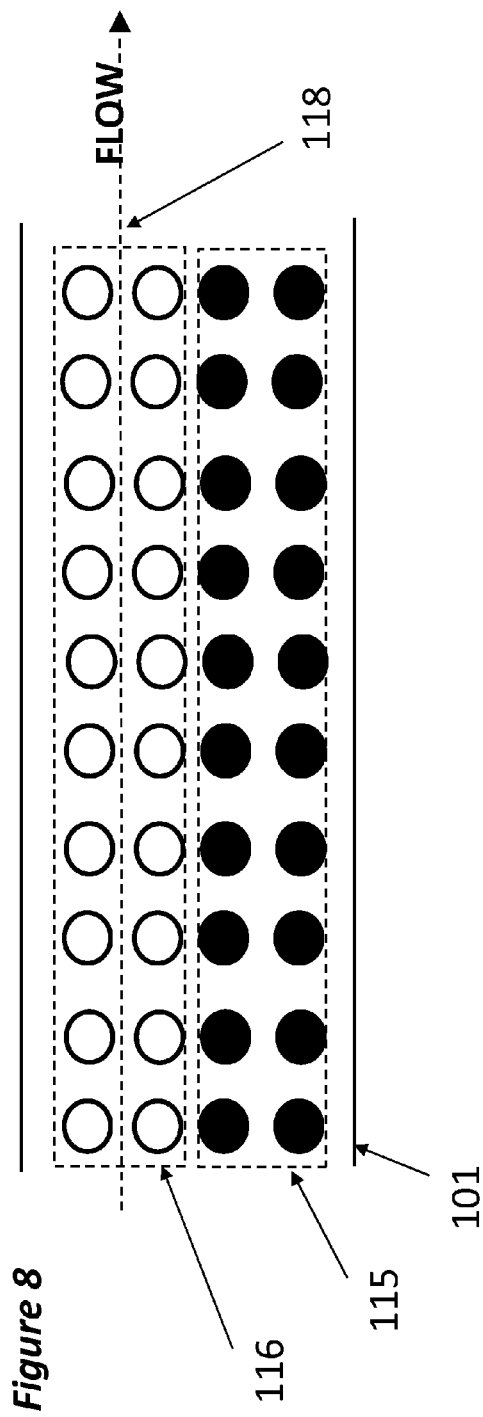
FIG. 8 illustrates a micro-fluidic device according to an embodiment of the disclosure, wherein the flow inside the channel is focused in a specific region.

FIG. 8 illustrates an embodiment of the disclosure. The micro-fluidic channel 101 comprises two groups 115, 116 of pillars. Each group 115, 116 of pillars is connected to a different electric power supply. By doing this, the propagation of the fluid inside the micro-fluidic channel 101 may be focused. The contact angle between the fluid and the pillars of group 115 is large while the contact angle between the fluid and the pillars of group 116 is relatively smaller. This allows the fluid to flow only through the area of the micro-fluidic channel 101 containing the pillars of group 116. As illustrated in FIG. 8, the flow of the fluid in the micro-fluidic device 100 is indicated by arrow 118.

In a third aspect of the disclosure, a sensing system for detecting bioparticles includes a micro-fluidic device according to any of the described embodiments, a radiation source for radiating the micro-fluidic device, and a detector for detecting SERS signals or surface plasmon resonance from the micro-fluidic device.

The system comprises a micro-fluidic device as presented in the first or second aspect of the disclosure, a radiation source, and a detector. The radiation source may be a monochromatic light source such as a laser. The detector may be a surface plasmon resonance detector or a detector for detecting SERS signals.

According to embodiments of the disclosure, the micro-fluidic channel 101 comprises 1) pillars with particles 140, such as plasmonic nanoparticles or SERS particles, at its surface, or 2) plasmonic pillars. When providing a fluid sample with bioparticles in the micro-fluidic channel 101, the capillary action created by the pillars in the micro-fluidic channel 101 ensures that the fluid sample propagates through the micro-fluidic channel 101. By controlling the electrowetting behaviour of each pillar, the propagation direction of the fluid can be controlled, e.g., stopped. It may be advantageous that the propagation of the fluid sample in the micro-fluidic channel can be controlled as this allows binding of target bioparticles to the particles 140 on the pillars or to the plasmonic pillars. When radiating the micro-fluidic channel 101, binding events can be detected using plasmonic resonance or SERS detection techniques.

When plasmonic nanoparticles are present on the surface of the pillars in the micro-fluidic channel, the plasmonic nanoparticles may be radiated with a light source. If one or more target bioparticles in the fluid sample binds with one or more of the immobilized receptor molecules present on the plasmonic nanoparticles, the surface plasmon resonance of the plasmonic nanoparticles changes, causing a change in an optical property relative to the optical property when one or more target bioparticles have not bound to the immobilized receptor molecules. The change indicates the presence of target bioparticles and enables detection.

When SERS nanoparticles are present on the surface of the pillars in the micro-fluidic channel, the SERS nanoparticles may be radiated with a light source. If one or more target bioparticles in the fluid sample binds with one or more of the immobilized receptor molecules present on the SERS nanoparticles, a SERS signal can be detected. Analysis of the SERS signal may indicate the presence of target bioparticles. It may be advantageous that without sample processing, a detection on the fluid sample can be done.

When the pillars located on the surface of the micro-fluidic channel are plasmonic pillars, the plasmonic pillars may be radiated with a light source. If one or more target bioparticles in the fluid sample binds with one or more of the immobilized receptor molecules present on the plasmonic pillars, the surface plasmonic resonance of the plasmonic pillars changes, causing a change in an optical property relative to the optical property when one or more target bioparticles have not bound to the immobilized receptor molecules. The change indicates the presence of target bioparticles and enables detection.

According to an embodiment of the disclosure, the SERS detector is a Raman spectrometer capable of detecting or recording a SERS signal. In a particular embodiment of the disclosure, the detector is a holographic dispersive gratings or a CCD multichannel detector. According to an embodiment of the disclosure, the plasmonic resonance detector may be a detector capable of detecting a change in the reflectivity or a change in the angle of a plasmonic resonance signal.

The system for sensing or detecting target bioparticles may further comprise a computing unit for analyzing and/or displaying plasmonic resonance or SERS signals.

Fabrication Steps

The micro-fluidic device as presented in the different aspects of the disclosure may be fabricated using standard CMOS processing techniques. This is illustrated in FIGS. 10a to 10f. A silicon substrate 200 with through-silicon vias (TSVs) 201 may be provided. A lithographic patterning step may be performed on the substrate to create the part of the micro-fluidic channel with the pillars. A metal layer 202 may be deposited to cover the surface of the substrate. Optionally, a dielectric layer and/or a hydrophobic layer may be provided on the metal layer. Thereafter, an etching step may be performed to separate the pillars from each other. The etching step is performed to isolate the metal layer of each pillar. The TSVs in the substrate should be provided at a position in the substrate so as to create a connection between the metal layer of each pillar and a TSV. In a final step, the substrate may be attached to a closing lid 203.

The invention claimed is:

1. A micro-fluidic device comprising:
   a micro-fluidic channel having an inner surface;
   a plurality of pillars positioned along a length of the inner surface of the micro-fluidic channel, wherein the plurality of pillars is configured for creating a capillary action in the micro-fluidic channel when a fluid is present in the micro-fluidic channel, and wherein the plurality of pillars is separated along a length of the inner surface of the micro-fluidic channel by a region that does not include pillars, wherein the region is defined at least in part by a first surface of the inner surface of the micro-fluidic channel and an opposing second surface of the inner surface of the micro-fluidic channel, wherein the first surface of the region is defined at least in part by a hydrophobic layer and the second surface of the region is defined at least in part by a hydrophilic layer; and
   a plurality of electric power supplies, wherein each electric power supply is suitable for generating a different voltage,
   and wherein each pillar is connected to a different electric power supply.

2. The micro-fluidic device according to claim 1, wherein each pillar includes a conductive core connected to a respective electric power supply.

3. The micro-fluidic device according to claim 2, wherein a dielectric layer covers a surface of the conductive core.

4. The micro-fluidic device according to claim 3, wherein at least one of a surface of the conductive core or a surface of the dielectric layer is covered with a hydrophobic layer.

5. The micro-fluidic device according to claim 1, wherein each pillar includes a core, and wherein a surface of the core is covered with a metal layer that is connected to a respective electric power supply.

6. The micro-fluidic device according to claim 5, wherein a surface of the metal layer is covered with a dielectric layer.

7. The micro-fluidic device according to claim 6, wherein a surface of the dielectric layer is covered with a hydrophobic layer.

8. The micro-fluidic device according to claim 1, wherein a selector connects each pillar to a respective electric power supply.

9. The micro-fluidic device according to claim 8, wherein the selector includes at least one transistor.

10. The micro-fluidic device according to claim 1, wherein each electric power supply is configured to generate a pulsed electric voltage.

11. The micro-fluidic device according to claim 1, wherein a surface of each pillar includes at least one of plasmonic nanoparticles or SERS nanoparticles.

12. The micro-fluidic device according to claim 1, wherein the inner surface of the micro-fluidic channel is defined at least in part by a first surface and an opposing second surface, wherein the plurality of pillars, outside of the region that does not include pillars, extends from the first surface, and wherein the second surface is defined at least in part by a reference electrode coupled to a ground potential.

13. The micro-fluidic device according to claim 1, wherein an aspect ratio of the plurality of pillars is defined as a height of a respective pillar divided by a diameter of the respective pillar, and wherein the aspect ratio ranges between 5 and 100.

14. A micro-fluidic device comprising:
a micro-fluidic channel having an inner surface;
a plurality of pillars positioned along an inner surface of the micro-fluidic channel, wherein the plurality of pillars is configured for creating a capillary action in the micro-fluidic channel, and wherein the plurality of pillars is separated along a length of the inner surface of the micro-fluidic channel by a region that does not include pillars, wherein the region is defined at least in part by a first surface of the inner surface of the micro-fluidic channel and an opposing second surface of the inner surface of the micro-fluidic channel, wherein the first surface of the region is defined at least in part by a hydrophobic layer and the second surface of the region is defined at least in part by a hydrophilic layer; and
at least one electric power supply,
wherein the plurality of pillars are grouped into at least two groups of pillars, wherein each group of pillars includes at least two pillars, and wherein all the pillars of at least one group of pillars are connected to the at least one power supply.

15. The micro-fluidic device according to claim 14, wherein each pillar connected to the at least one power supply includes a conductive core connected to the at least one power supply, wherein a dielectric layer covers one or more of the conductive cores, and wherein a hydrophobic layer covers one or more of the dielectric layer or conductive cores.

16. The micro-fluidic device according to claim 14, wherein each pillar connected to the at least one power supply includes a core, wherein a surface of each core is covered with a metal layer that is connected to the at least one power supply, wherein a dielectric layer covers one or more of the metal layers, wherein a hydrophobic layer covers one or more of the dielectric layers.

17. The micro-fluidic device according to claim 14, wherein a selector connects the pillars to the at least one power supply, wherein the selector includes at least one transistor.

18. The micro-fluidic device according to claim 14, wherein each pillar is further connected to biosensing circuitry for sensing an electrochemical signal.

* * * * *